United States Patent [19]

Hoffman et al.

[11] Patent Number: 4,492,752
[45] Date of Patent: Jan. 8, 1985

[54] METHOD FOR DISCRIMINATING BETWEEN UNSTAINED AND ABSORBING DYE STAINED CELLS

[75] Inventors: Robert A. Hoffman; Stephen H. C. Ip, both of Mansfield, Mass.

[73] Assignee: Ortho Diagnostics Systems Inc., Raritan, N.J.

[21] Appl. No.: 414,683

[22] Filed: Sep. 3, 1982

[51] Int. Cl.$^3$ .............. G01N 33/50; G01N 33/52; G01N 33/54; G01N 21/47
[52] U.S. Cl. ................... 435/7; 250/461.2; 356/39; 424/3; 436/63; 436/519; 436/805
[58] Field of Search .............. 436/63, 805, 519; 250/461.2; 356/39; 435/7; 424/3

[56] References Cited

U.S. PATENT DOCUMENTS

| | | | |
|---|---|---|---|
| 3,659,946 | 5/1972 | Kozawa | 356/104 |
| 3,684,377 | 8/1972 | Adams | 356/36 |
| 3,785,735 | 1/1974 | Friedman | 356/39 |
| 4,172,227 | 10/1979 | Tyrer | 250/461.2 |
| 4,174,952 | 11/1979 | Cannell | 435/7 X |
| 4,193,980 | 3/1980 | Clason | 436/63 X |
| 4,202,625 | 5/1980 | Weiner | 356/39 |
| 4,325,706 | 4/1982 | Gershman | 356/39 X |
| 4,336,029 | 6/1982 | Natale | 250/461.2 X |
| 4,343,782 | 8/1982 | Shapiro | 436/63 X |

OTHER PUBLICATIONS

Ortho Instruments Protocol No. 8, "Cytographic Analysis of Con–A Receptor Sites in Plasmacytoma Cells", Ortho Instruments, 410 University Ave., Westwood, Mass. 02090.
M. R. Melamed et al., Science, 163, 285–286 (1969).
W. P. Drake et al., Transplantation, 14 (1), 127–130 (1972).
F. Traganos et al., The Journal of Histochemistry and Cytochemistry, 25 (1), 46–56 (1977).
J. F. Leary et al., The Journal of Histochemistry and Cytochemistry, 24 (12), 1249–1257 (1976).

Primary Examiner—Sidney Marantz
Attorney, Agent, or Firm—Audley A. Ciamporcero, Jr.; Mark A. Hofer

[57] ABSTRACT

Method for discriminating unstained cells from stained cells in a heterogeneous population. Specified cell types are stained with an absorbing stain and all cells are passed through the class of flow cytometry instrumentation employing focused collimated light sources. Detection of low angle and wide angle light scatter permits differentiation between the cell types on the basis that cells stained with an absorbing stain produce comparatively less low angle light scatter and comparatively more wide angle light scatter than do unstained cells.

3 Claims, 3 Drawing Figures

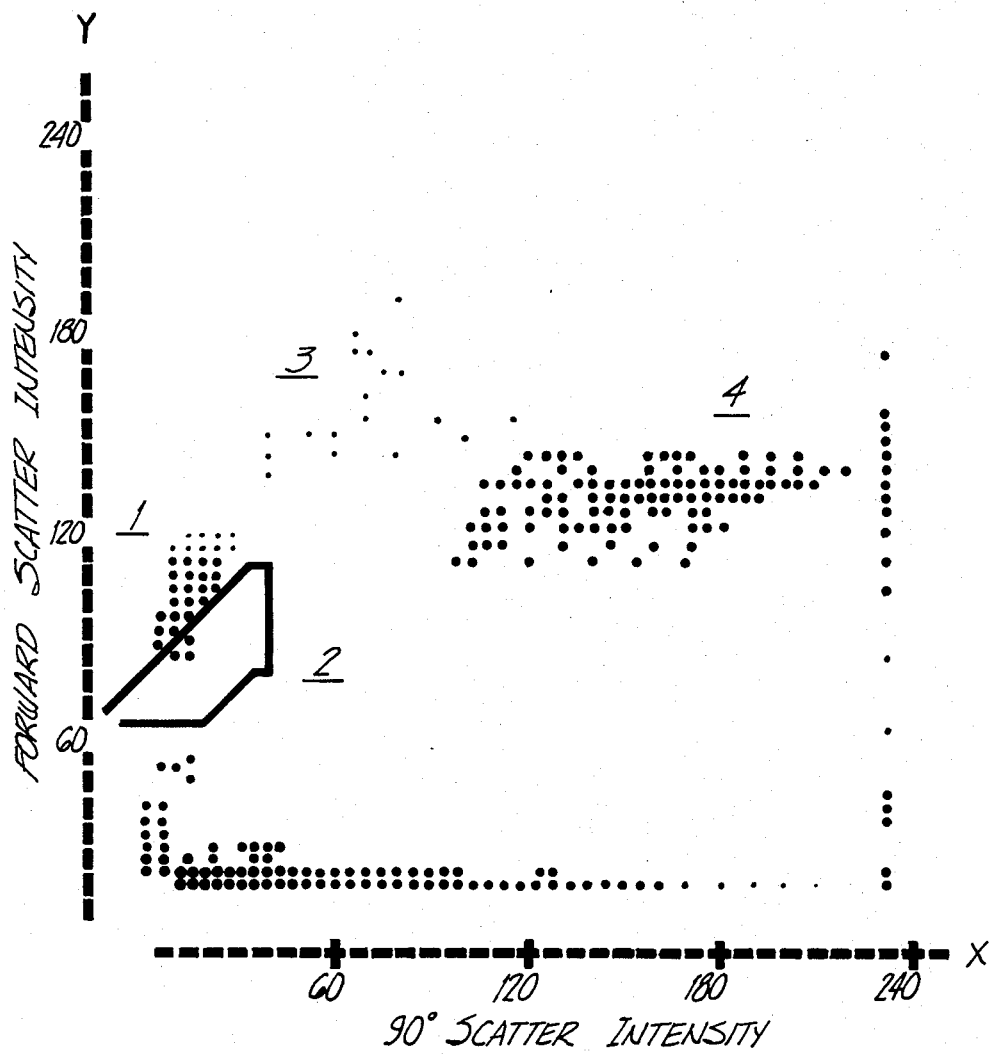

METHOD FOR DISCRIMINATING BETWEEN UNSTAINED AND ABSORBING DYE STAINED CELLS

FIELD OF THE INVENTION

This invention relates to a method for discriminating between unstained cells and cells stained with a light absorbing surface stain in a heterogeneous mixture based on the parameters of low angle and wide angle light scatter. More particularly, this invention is intended for use in light based flow cytometry instrumentation.

BACKGROUND OF THE INVENTION

With the advent of the use of flow cytometry instrumentation in clinical and research environments, it has become concurrently necessary for purposes of toxicology, diagnosis, the identification of preferred hybridoma cell lines and the like to be able to discriminate between cell types in a heterogeneous cell population. Historically this has been accomplished by either employing stains specific for viable cells as opposed to nonviable cells, i.e. the vital type stains, or by the measurement of multiple parameters such as size, degree of fluorescence exhibited and the like in an effort to distinguish between the effects of a stain applied generally to all the cells in the mixture.

For instance, in an article by Dr. Myron R. Melamed entitled "Cytotoxic Test Automation: A Live Dead Cell Differential Counter" (Science, 163:285-286, 1969) a method was described whereby a cell spectrofluorometer was employed for the automatic discrimination and enumeration of live and dead cells in a cytotoxic test. The vital indicator employed was trypan blue because nonviable cells take up trypan blue and hence become stained while living cells exclude the dye and thus remain unstained. Since trypan blue effectively absorbs light, a measurement of absorption can be correlated to the percentage of stained or nonviable cells versus unstained viable cells.

It is an object of the present invention to provide a method which does not rely on the viability of cells and a resultant differential uptake of a vital type stain but rather is capable of discriminating between viable cells by use of a non-absorbence measurement technique.

Differentiation of cells based on different dye uptakes and measurements of scatter and absorption has been described by Friedman et al. in U.S. Pat. No. 3,785,735. Specifically illustrated in that patent is the differentiation of live and dead cells based upon the different uptakes of a vital stain such as trypan blue. It was found that dead cells which were stained by trypan blue exhibited characteristics of high absorbence and low scatter whereas live cells exhibited low absorbence and high scatter characteristics. Friedman measured absorbence by placing the detectors at a wide angle to the incident illuminating light beam in an effort to reduce noise signals apparently greater with direct (zero angle) absorbence measurement. Friedman relies on absorbence and scatter measurements in order to discriminate between live and dead cells, he does not teach how differentiation between different, live cell types may be accomplished without reliance on absorbence measurements.

It is an object of the present invention to provide a method whereby cells stained with an absorbing surface stain and unstained cells present in a heterogeneous mixture may be differentiated by reliance on low angle and wide angle scatter measurements but without reliance on additional absorbence measurements. In fact, scatter and absorbence may be shown to be inversely related in that the more light that is absorbed by a surface, the less light is available for scatter. Thus, Friedman claims that dead cells (stained by trypan blue) absorb more light than unstained cells and thereby implies a characteristically lower scatter measurement with a stained cell than with an unstained cell. It has been discovered that in fact, the wide angle measurement of a cell stained with an absorbing type stain demonstrates increased scatter over that produced by unstained cells. It is consequently an object of the present invention to utilize this discovery in discriminating between stained and unstained cells.

The use of an absorbing dye to detect cytoplasmic immumoenzyme staining of a viral antigen has been described by Leary et al, J. Histochem. Cytochem. 24, 1249 (1976). Cells containing virus were fixed in formaldehyde and then reacted with an antibody against the virus. A second antibody conjugated to the enzyme peroxidase and reactive with the first antibody was then reacted with the cells. When the substrate diaminobenzidine dihydrochloride was then reacted with the cells, a brown reaction product was deposited in those cells with the peroxidase enzyme, and hence those cells containing antibody against the virus. The presence of brown reaction product was detected by analyzing the cells on an ORTHO CYTOFLUOROGRAF* Flow Cytometer with an argon ion laser. On the CYTOFLUOROGRAF axial light loss, angular range 0°-1° relative to the laser beam, (called "low angle scatter" by Leary et al) and forward light scatter, angular range 1°-19° relative to the laser beam, (called "wide angle scatter" by Leary et al) were measured. Reactive cells showed less forward light scatter and more axial light loss than unreactive cells.

*Trademark

A similar effect is reported for light-absorbing stain on the surface of cells in Ortho Protocol Number 8, published by and available from Ortho Diagnostic Systems Inc. In this protocol, "Cytographic Analysis of Con-A Receptor Site in Plasmacytoma Cells," a method is described for immunoperoxidase staining of concanavalin A on the surface of cells. The staining results in a light-absorbing red stain on the surface of the cells. Axial light loss and forward light scatter from a helium neon laser were measured on a CYTOGRAF 6300A*. Stained cells showed markedly decreased forward light scatter, while axial light loss did not change greatly.

*Trademark

An object of the present invention is to replace the relatively insensitive axial light loss measurement with a measurement of light scattered at very wide angles (approximately 55° to 125° as measured on the CYTOFLUOROGRAF). Wide angle light scatter has been found by us to be significantly affected by the presence of light-absorbing stains in or on the surface of cells.

Other conventional methods of cell differentiation have been based on the measurement of different fluorescent characteristics of cells uniformly stained with a single type of fluorochrome. For example, U.S. Pat. No. 3,684,377 to Adams et al. describes a method of analyzing living white blood cells from other blood components utilizing various compositions comprising, in part, acridine orange as the fluorochrome. The cells are subjected to blue laser illumination and detection of green fluorescence provides a distinguishing feature between white blood cells and other blood components. Combination of this information with the detection of red fluorescence emitted from individual white cells, permits discrimination between white cell types. It is an object of the present invention to provide a method which does not depend upon the detection of multiple fluorescent characteristics in order to effectuate cell type differentiation.

Differentiation between blood components has also been accomplished by two dimensional signal analysis of a detected scatter signal as the cells passed through a focused collimated light source. Such a method is described in U.S. Pat. No. 4,202,625 to Weiner et al. which describes methods and apparatus whereby blood components, specifically red blood cells and platelets, may be distinguished. Weiner, however, does not teach how scatter measurements in conjunction with absorbence dyes may be used to differentiate cell types. It is an object of the present invention to provide such methodology.

SUMMARY OF THE INVENTION

In accordance with the objects of the present invention, methods are provided for the differentiation of cell types in a heterogeneous sample having a mixture of unstained cells and cells stained with a light absorbing surface or cytoplasmic stain. Differentiation may be accomplished by detection of low angle and wide angle light scatter in that class of blood analysis equipment utilizing optical systems to irradiate and analyze individual blood cells, i.e., the so called flow cytometry instrumentation. Low angle scatter is ideally defined as scatter within the range 1° to 19° from the incident laser beam, while wide angle scatter is ideally defined as scatter within the range of 60° to 120° or greater from the incident laser beam. (Note that Leary, cited above, inaccurately describes the range 1° to 19° as wide angle scatter.) Specified cell types may be stained by employing a serologically specific antibody labeled with a marker such as an enzyme. Such an antibody will advantageously react only with a particular antigen and will preferably be of monoclonal origin in order to reduce crossreactivity and non-specific binding. The antibody is advantageously chosen to react with antigens present only on the cell type desired to be stained. Subsequent reaction of the enzyme with a suitable substrate will ideally result in the deposition of an insoluble product on the surface of the cell. This insoluble product is advantageously chosen to absorb or attenuate incident light.

Thus, measurement of the stained and unstained cells, in particular their low angle and wide angle light scattering characteristics, will permit their differentiation based on the discovery that cells stained with an absorbing surface or cytoplasmic stain produce comparatively less low angle scatter and comparatively more wide angle light scatter than do unstained cells.

BRIEF DESCRIPTION OF THE DRAWINGS

FIG. 3 shows the saline control results of the experiment described in FIG. 2.

BEST MODE FOR CARRYING OUT THE INVENTION

Although it will be apparent that the principles of the present invention may be applied to a variety of optical blood analysis systems, a preferred mode of application relates to those systems employing hydrodynamic focusing wherein the cells are passed through a narrow fluid vortex approximately 1 cell wide, a cell at a time at a very high rate past a focused, collimated, or laser light source for illumination of the single cells. Transmitted radiation is physically blocked by a contrived obstruction that matches the light beam cross-sectional profile after exiting the flow chamber containing the hydrodynamically focused cells in the absence of cells. Scattered radiation passing around this contrived obstruction at low forward angles is detected as well as light scattered at wide angles from the incident light source typically at 90°. One such instrument is the Ortho Spectrum III TM available from Ortho Diagnostic Systems Inc., Rt. 202, Raritan, N.J.

Cells to be detected in the heterogeneous sample are stained by applying an absorbing or attenuating type stain directly to their surface or cytoplasm or forming such a stain by enzymatic activity. Identification of the desired cells is preferably accomplished by employing the so called monoclonal antibodies which are chosen to have a specificity for antigens present on the surface of only those cells which are to be stained. Thus, attachment of a label such as the absorbing dye itself or an enzyme to the monoclonal antibody results in the indirect attachment of the label to the desired cell type. In the preferred mode, an enzyme is used so that addition of the appropriate substrate under conditions which promote the enzymatic reaction results in the deposition of a product on the surface or in the cytoplasm of the cell. This product then becomes the absorbing dye. Comparison of the altered light scattering characteristics of absorbing dye stained cells versus unstained cells shows that on low angle scattering detection, unstained cells will typically show greater scatter than the unstained cells. Conversely, detection of scattering at wide angles, preferably at 90° to the incident light, shows that unstained cells will characteristically exhibit less scatter than those cells stained with the absorbing dye on their surface. Thus, selected cell types may be differentiated from other cells in a heterogeneous cell population.

Figure 1:
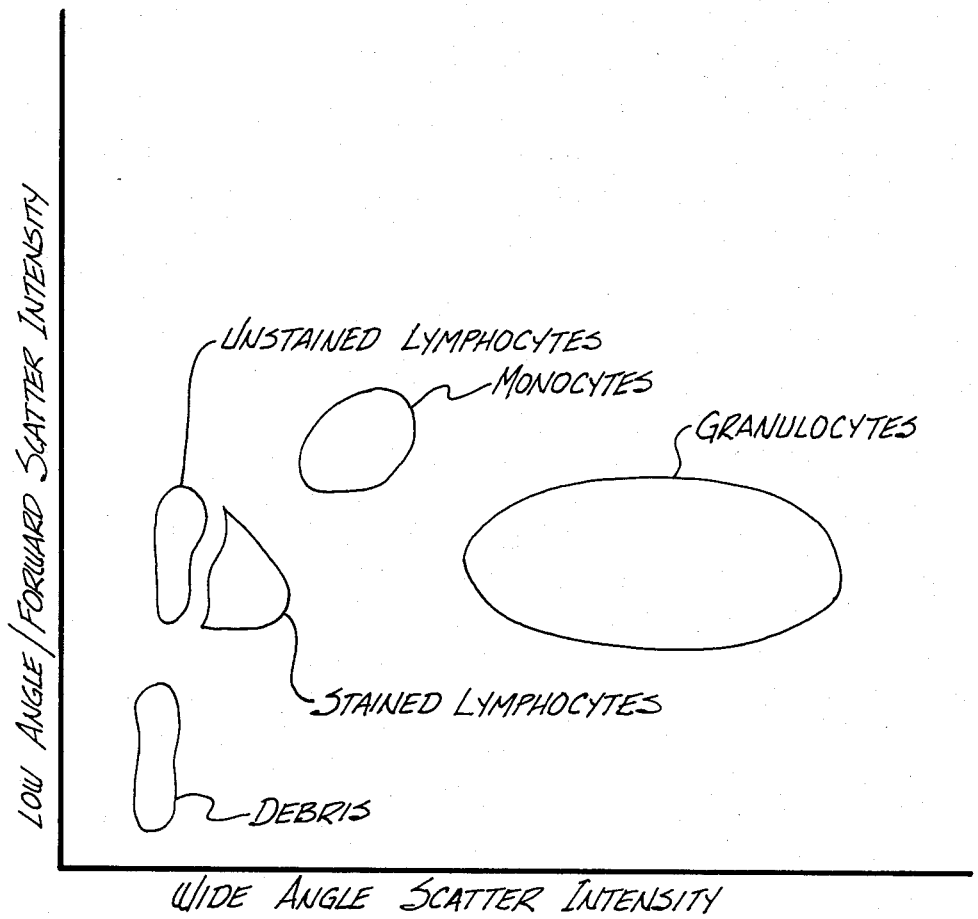
FIG. 1 schematically shows a light scatter cytograph of stained lymphocytes in a whole blood preparation.

FIG. 1 shows a hand drawing illustrating the expected two dimensional histogram of a whole blood sample when analyzed on an Ortho Spectrum III TM or Cytofluorograph TM (both available from Ortho Diagnostic Systems Inc.), wherein a specified lymphocyte subpopulation is stained with an absorbing stain. The debris cluster will typically comprise red cell ghosts and platelets.

Figure 2:
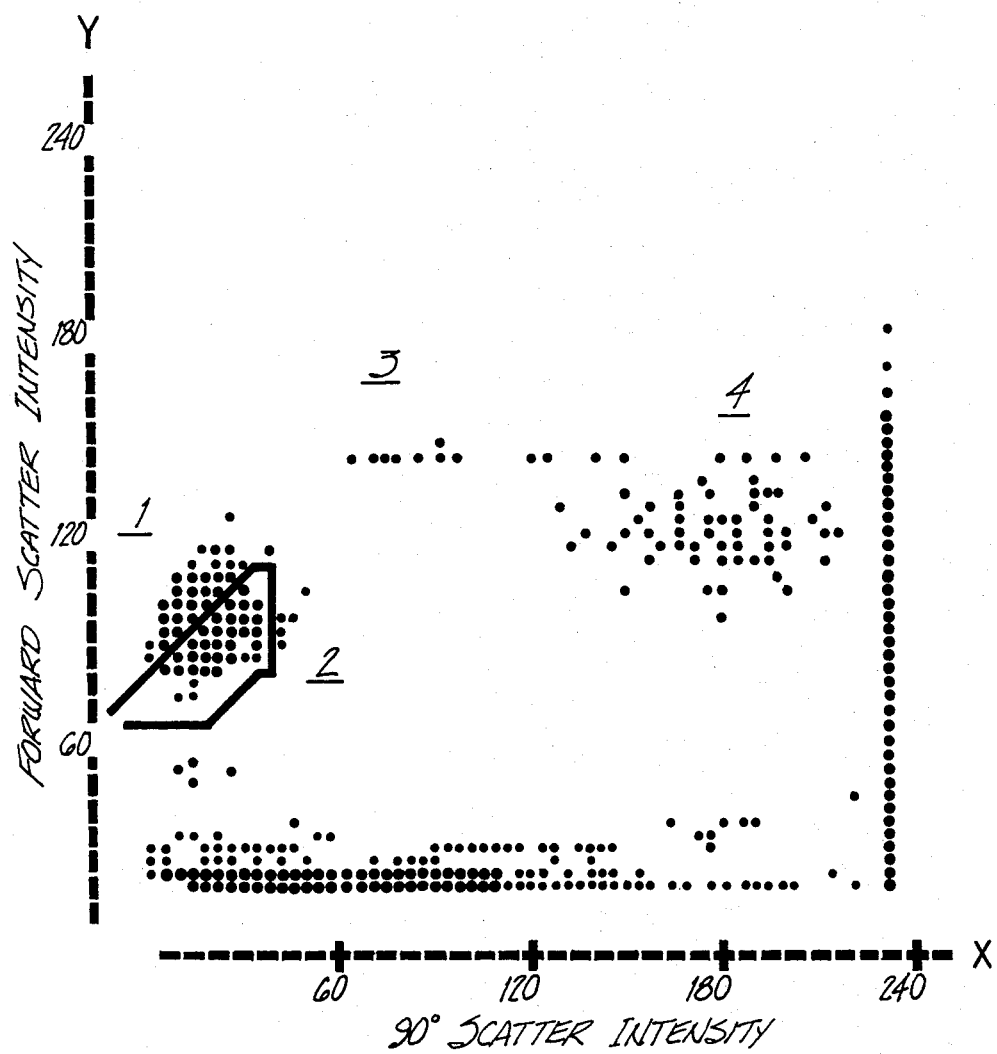
FIG. 2 shows the experimental results of immunoperoxidase staining of a whole blood sample when reacted with OKT3 TM, anti-thymus-lymphocyte monoclonal antibody.

FIG. 2 shows the results of an experiment wherein the thymus differentiated lymphocytes, i.e. the so called T-cells, are detected in the heterogeneous whole blood cell mixture. Monoclonal antibody OKT3 TM (also available from Ortho Diagnostic Systems Inc., Route 202, Raritan, N.J.) specific for T-cells, was reacted with the whole blood sample and because of serological specificity, the serological reaction was limited to the T-lymphocyte population. The cells were then subsequently reacted with peroxidase conjugated goatantmouse antibody specific for the mouse derived monoclonal antibody OKT3 TM. Addition of the peroxidase substrate, hydrogen peroxide and 4-chloro-1-naphthol, produced a black absorbing stain on the surface of the T-lymphocytes. Analysis of the sample through the Ortho Spectrum III TM produced the scatter characteristics shown in FIG. 2. The saline control sample revealed the scatter characteristics shown in FIG. 3. Both figures show clusters corresponding to unstained lymphocytes 1, monocytes 3 and granulocytes 4 and debris 5. In FIG. 2, the stained lymphocytes are apparent in cluster 2 while in FIG. 3, the control sample, as expected, the cluster due to stained cells is absent. Consequently, the method effectively discriminates thymus differentiated cells in a mixture of leukocytes present in a whole blood sample.

As an example of the effect of a cytoplasmic absorbing stain, blood cells were stained in the nitroblue tetraxolium (NBT) test as follows. Whole blood was incubated with NBT in buffered saline at 37° for 15 minutes. Actively phagocytizing leukocytes ingest NBT and reduce it to an insoluble blue (hence red light absorbing) product. To induce leukocytes to phagocytize, 12-O-tetradecanoylphorbol-13-acetate (TPA) was added to some samples. After the incubation with NBT, and in some cases TPA, the red cells were lysed and the sample was analyzed on an ORTHO CYTOFLUOROGRAF FC200. Forward light scatter (1°–19°) and wide angle light scatter (55°–225°) were measured on the CYTOFLUOROGRAF with a helium neon laser as the light source. Results showed that samples incubated with NBT alone had light scatter characteristics typical of unaltered leukocytes. When TPA was added, however, the granulocytes had greatly decreased forward light scatter and greatly increased wide angle light scatter. This effect was apparently due to the presence of NBT in these cells.

It will be understood that the foregoing sets forth the principles of the present invention and features of a preferred embodiment, but that numerous alternative embodiments will occur to those of ordinary skill in the art without departure from the spirit or scope of the principles of the present invention.

What is claimed is:

1. A method for discriminating, in a mixed cell sample, between unstained cells and cells stained with a cell surface or cytoplasmic stain using low angle and wide angle light scatter measurements in light based flow cytometry instrumentation comprising the steps of:
   (a) staining some cells in the mixed sample with a light absorbing stain;
   (b) providing the mixed sample having stained and unstained cells past a focused light source;
   (c) detecting low angle and wide angle light scatter as the cells pass the light source; and
   (d) discriminating between stained and unstained cells on the basis that cells with a light absorbing stain produce comparatively less low angle light scatter and comparatively more wide angle light scatter than do unstained cells.

2. A method for discriminating, in a mixed cell sample, between unstained cells and cells stained with a cell surface or cytoplasmic stain using low angle and wide angle light scatter measurements in light based flow cytometry instrumentation comprising the steps of:
   (a) staining some cells in the mixed sample with a light absorbing stain;
   (b) providing the mixed sample having stained and unstained cells past a focused light source;
   (c) detecting low angle and wide angle light scatter as the cells pass the light source; and
   (d) discriminating between stained and unstained cells on the basis that cells with a light absorbing stain produce comparatively less low angle light scatter and comparatively more wide angle light scatter than do unstained cells,
   wherein the staining step (a) comprises:
   (1) reacting the cells to be stained with a first antibody specific for the cells to be stained, said antibody having a first label selected from the group consisting of absorbing dyes, enzymes, and a second antibody specific for the first antibody which is reacted with the first antibody after the first antibody has been allowed to react with the cells to be stained, said second antibody having a second label selected from the group consisting of absorbing dyes and enzymes; and
   (2) additionally providing, when either the first or second label is an enzyme, a substrate for reacting with the enzyme whereby an insoluble, light absorbing product is produced at the site of the label.

3. The method as provided in claim 2 wherein the enzyme is peroxidase and the substrate is hydrogen peroxide and 4-chloro-1-naphthol.

* * * * *